US012260607B2

(12) United States Patent
Mutter et al.

(10) Patent No.: US 12,260,607 B2
(45) Date of Patent: Mar. 25, 2025

(54) AUGMENTED DIGITAL MICROSCOPY FOR LESION ANALYSIS

(71) Applicants: THE BRIGHAM AND WOMEN'S HOSPITAL, INC., Boston, MA (US); CHARITE UNIVERSITATSMEDIZIN BERLIN, Berlin (DE)

(72) Inventors: George L. Mutter, Boston, MA (US); Peter Hufnagl, Berlin (DE); Sebastian Lohmann, Berlin (DE); David James Papke, Jr., Boston, MA (US)

(73) Assignees: THE BRIGHAM AND WOMEN'S HOSPITAL, INC., Boston, MA (US); CHARITE UNIVERSITATSMEDIZIN BERLIN, Berlin (DE)

(*) Notice: Subject to any disclaimer, the term of this patent is extended or adjusted under 35 U.S.C. 154(b) by 752 days.

(21) Appl. No.: 17/414,010

(22) PCT Filed: Dec. 16, 2019

(86) PCT No.: PCT/US2019/066579
§ 371 (c)(1),
(2) Date: Jun. 15, 2021

(87) PCT Pub. No.: WO2020/124084
PCT Pub. Date: Jun. 18, 2020

(65) Prior Publication Data
US 2022/0050996 A1 Feb. 17, 2022

Related U.S. Application Data

(60) Provisional application No. 62/818,446, filed on Mar. 14, 2019, provisional application No. 62/780,224, filed on Dec. 15, 2018.

(51) Int. Cl.
G06K 9/00 (2022.01)
G06T 7/00 (2017.01)
(Continued)

(52) U.S. Cl.
CPC .......... *G06V 10/426* (2022.01); *G06T 7/0014* (2013.01); *G06V 20/69* (2022.01);
(Continued)

(58) Field of Classification Search
CPC ......... G06T 2207/30024; G06T 7/0012; G06T 2207/10056; G06T 2207/10081;
(Continued)

(56) References Cited

U.S. PATENT DOCUMENTS 8,280,132 B2 * 10/2012 Madabhushi ........ G06V 20/695
382/128
2006/0015952 A1 1/2006 Filvaroff
(Continued)

FOREIGN PATENT DOCUMENTS

WO WO-2018186789 A1 * 10/2018 ........... G06K 9/0014
WO WO-2021080007 A1 * 4/2021 ........... G01N 21/636

OTHER PUBLICATIONS

P. Baran et al., "High-Resolution X-Ray Phase-Contrast 3-D Imaging of Breast Tissue Specimens as a Possible Adjunct to Histopathology," in IEEE Transactions on Medical Imaging, vol. 37, No. 12, pp. 2642-2650, Dec. 2018, doi: 10.1109/TMI.2018.2845905. (Year: 2018).*

(Continued)

*Primary Examiner* — Gregory A Morse
*Assistant Examiner* — Kevin M Coomber
(74) *Attorney, Agent, or Firm* — Tarolli, Sundheim, Covell & Tummino LLP

(57) ABSTRACT

Systems and methods are provided for augmenting digital analysis of lesions. An image of tissue having a glandular
(Continued)

epithelial component is generated. The image represents a plurality of medium-scale epithelial components. For each of a plurality of cells within the image, a representative point is identified to provide a plurality of representative points for each of the plurality of medium-scale epithelial components. For each of a subset of the plurality of medium-scale epithelial components, a graph connecting the plurality of representative points is constructed. A plurality of classification features is extracted for each of the subset of medium-scale epithelial components from the graph constructed for the medium-scale epithelial component. A clinical parameter is assigned to each medium-scale epithelial component according to the extracted plurality of classification features.

9 Claims, 5 Drawing Sheets

(51) Int. Cl.
  *G06V 10/426* (2022.01)
  *G06V 20/69* (2022.01)
  *A61B 90/20* (2016.01)
(52) U.S. Cl.
  CPC ............ *G06V 20/698* (2022.01); *A61B 90/20* (2016.02); *G06T 2207/10056* (2013.01); *G06T 2207/10081* (2013.01); *G06T 2207/30024* (2013.01)
(58) Field of Classification Search
  CPC .... G06T 7/0014; G06V 20/69; G06V 10/426; G06V 20/698; G16H 10/40; G16H 30/40; A61B 90/20; A61B 5/064; A61B 2090/3762; A61B 2034/2055
  See application file for complete search history.

(56) References Cited

U.S. PATENT DOCUMENTS

| | | | |
|---|---|---|---|
| 2006/0078926 | A1 | 4/2006 | Marcelpoil et al. |
| 2008/0031521 | A1* | 2/2008 | Can .................. G06T 7/0012 382/173 |
| 2013/0194312 | A1* | 8/2013 | Yoshioka ............. G06F 3/0485 345/672 |
| 2013/0230230 | A1 | 9/2013 | Champalimaud et al. |
| 2016/0335478 | A1* | 11/2016 | Bredno ................ A61B 34/74 |
| 2017/0076442 | A1 | 3/2017 | Schoenmeyer et al. |
| 2017/0076448 | A1* | 3/2017 | Chen ...................... G06T 7/12 |
| 2018/0232883 | A1* | 8/2018 | Sethi .................... G16H 30/40 |
| 2018/0247107 | A1* | 8/2018 | Murthy ............... G06V 20/698 |

OTHER PUBLICATIONS

A. B. Tosun and C. Gunduz-Demir, "Graph Run-Length Matrices for Histopathological Image Segmentation," in IEEE Transactions on Medical Imaging, vol. 30, No. 3, pp. 721-732, Mar. 2011, doi: 10.1109/TMI.2010.2094200 (Year: 2011).*

PCT Search Report and Written Opinion for corresponding application Serial No. PCT/US2019/066579 with an International filing date of Dec. 16, 2019 mailed Feb. 21, 2020, pp. 1-17.

* cited by examiner

AUGMENTED DIGITAL MICROSCOPY FOR LESION ANALYSIS

RELATED APPLICATIONS

This application claims priority from U.S. Provisional Patent Application No. 62/780,224, filed Dec. 15, 2018 and entitled "SYSTEM AND METHOD FOR DIGITAL LESION ANALYSIS". This application claims priority from U.S. Provisional Patent Application No. 62/818,446, filed Mar. 14, 2019 and entitled "AUGMENTED DIGITAL MICROSCOPY FOR DIAGNOSIS OF ENDOMETRIAL NEOPLASIA", both of which are incorporated by reference in their entirety.

TECHNICAL FIELD

This invention relates to the field of medical diagnostics, and more specifically, to systems and methods for digital lesion analysis.

BACKGROUND

Examination of microscopic tissue sections by a trained pathologist is the basis of pathologic diagnoses used in disease classification and patient management. In its traditional form, a physical tissue section is stained with dyes or biomarker probes, using methods such as immunohistochemistry, and interpreted visually at an optical microscope by a pathologist who assigns a disease category, diagnosis, and when appropriate, a disease extent (e.g., margin involvement, size). Accuracy and precision of the diagnostic process is a combined function of the specimen sample, means of specimen visualization, applicable diagnostic criteria, and interpretive skills of the pathologist. Increased use of digital whole histologic slide images and computer viewing systems as a replacement for the optical microscope is a change in workflow that enables the current invention.

SUMMARY OF THE INVENTION

In accordance with an aspect of the present invention, a system includes an imager that provides an image of tissue having a glandular epithelial component. The image represents a plurality of medium-scale epithelial components. The system further includes a processor and a non-transitory computer readable medium storing instructions executable by the processor. The executable instructions include a cell identification component that identifies, for each of a plurality of cells within the image, a representative point to provide a plurality of representative points for each of the plurality of medium-scale epithelial components. A graph constructor constructs, for each of a subset of the plurality of medium-scale epithelial components, a graph connecting the plurality of representative points. A feature extractor determines, for each of the subset of medium-scale epithelial components, a plurality of classification features from the graph constructed for the medium-scale epithelial component. A machine learning model assigns a clinical parameter to each medium-scale epithelial component according to the extracted plurality of classification features.

In accordance with another aspect of the present invention, a method is provided. An image of tissue having a glandular epithelial component is generated. The image represents a plurality of medium-scale epithelial components. For each of a plurality of cells within the image, a representative point is identified to provide a plurality of representative points for each of the plurality of medium-scale epithelial components. For each of a subset of the plurality of medium-scale epithelial components, a graph connecting the plurality of representative points is constructed. A plurality of classification features is extracted for each of the subset of medium-scale epithelial components from the graph constructed for the medium-scale epithelial component. A clinical parameter is assigned to each medium-scale epithelial component according to the extracted plurality of classification features.

In accordance with yet another aspect of the present invention, an image of tissue having a glandular epithelial component is generated. The image represents a plurality of glands. A clinical parameter is assigned to a subset of the plurality of glands according to features extracted from the image. A spatial mapping of the subset of the plurality of glands is generated, with each gland in the spatial mapping represented by an indicator indicative of the clinical parameter assigned to the gland. The spatial mapping is displayed to a user at an associated display.

DETAILED DESCRIPTION

Figure 1:
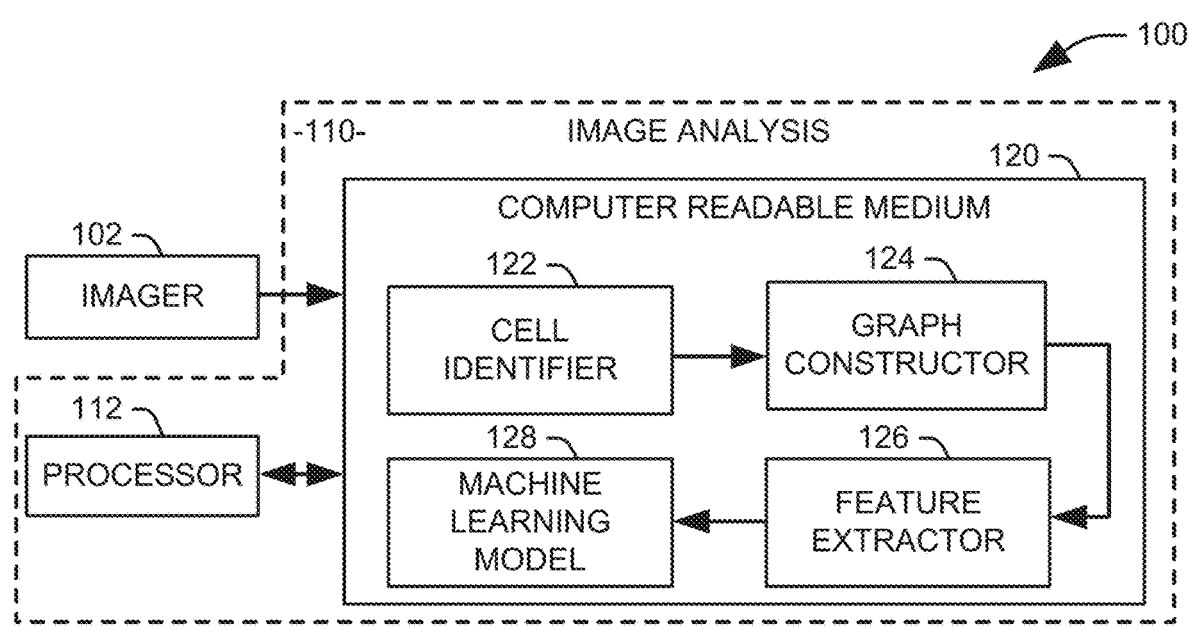
FIG. 1 illustrates a system for locating lesions in tissue in accordance with an aspect of the present invention.

A pathologist has to find the lesion before a diagnosis can be made, which is a special challenge in highly fragmented specimens, such as prostate chips and endometrial biopsy fragments, where multiple fragments are first screened in low magnification fields of view. Even when only one piece of tissue is present, the lesion may be focal. Pathologists address this by initially approaching a microscopic section at low magnification, screening quickly for particular areas that may represent a lesion. Once identified, such an area is viewed at higher magnification to make a diagnosis. Typically, ninety percent of the diagnostic effort is spent on less than ten percent of the entire slide.

Whole-slide digital imaging is a process where a high resolution zoomable montage of an actual tissue section is presented to a display device. Extensive downsampling of captured images for presentation in existing visual interfaces is especially problematic during this initial screening process of multiple fragments or large areas as one visual field. Although resolution during primary capture is often 20× or 40× magnification, current display devices limit what the pathologist is able to see. Particularly, the resolution of the presented image is poor at low magnification renderings where a downsampled single gland may be represented by only a few pixels on the screen. This is insufficient to see many of the cellular details necessary to recognize a lesion. Notably, at low display magnifications, such as when fullscreen displays 3-4 mm of linear distance, those features captured at high resolution in the full digital source image remain accessible to the computer, even though they cannot be seen by the viewer looking at the screen.

Accordingly, one implementation of the invention incorporates automated collection of small and large scale morphologic features within an image, such as a digital histologic, statistical processing of such data from that same slide into clinically or diagnostically meaningful parameters, and real-time, in-situ display of that classification information with the original histologic image. It can be implemented as a background image analysis function that drives "smart" summary display of relevant features in the viewable context of the original image. In this implementation, the system highlights specific diagnostic features individually and/or in meaningful combinations within the digital slide.

The term "image," as used herein, is intended to include any two-dimensional or three-dimensional array of intensity values or attenuation values representing electromagnetic radiation or detectable beams reflected from, emitted by, and/or passing through a region of interest. For example, the term "image" is intended to encompass optical microscopy, spectral and reflectance imaging, laser induced emission, and X-ray tomography.

The term "center," as used herein, is intended to include any spatial measure of central tendency within a two-dimensional or three-dimensional image. Accordingly, the "center" of an imaged structure can include an optical density centroid of the structure, the center of a minimum bounding box enclosing the structure, a geometric centroid of the structure, or geometric centroid of an idealized polygon or polyhedron representing the structure.

The phrase "medium-scale epithelial component," as used herein, refers to any one of whole glands, gland epithelial compartments, gland-stromal interfaces, luminal compartments.

The term "subset," as used herein, is intended to be used in the mathematic sense in which each set is a subset of itself. Where less than all of a set is intended, the term "proper subset" is used.

FIG. 1 illustrates a system 100 for locating lesions in tissue in accordance with an aspect of the present invention. The system 100 includes an imager 102 that provides an image of tissue having a glandular epithelial component, such that the image contains a plurality of medium-scale epithelial components. It will be appreciated that the imager 102 can include any appropriate system for generating an image of tissue in which the individual cells comprising medium-scale epithelial components can be seen. Examples include X-ray microtomographic imagers, scanning electron microscopes, digital optical microscopes, digital microscopes using other bands of electromagnetic radiation (e.g., infrared, spectral, ultraviolet), spectral and reflectance imaging, in vivo microscopy, light sheets, microscopy, laser induced emission ,and scanning probe microscopes (e.g., using scanning ion-conductance microscopy or scanning near-field optical microscopy).

The image generated at the imager 102 is provided to an image analysis system 110. The image analysis system 110 includes a processor 112 and a non-transitory computer readable medium 120 that stores instructions executable by the processor to assign one or more clinical parameters to individual medium-scale epithelial components within the image. A clinical parameter, as used herein, can be any continuous or categorical parameter that represents a biological state of the medium-scale epithelial component. In one example, the clinical parameter can be selected from a number of classes, including some combination of a "normal" class, a "precancerous" class, a "malignant" class, a "benign" class, and an "unsure" class. Alternatively, the clinical parameter can represent a probability that a biological state of interest, such as neoplasia generally or cancer specifically, is present in the medium-scale epithelial component. The parameter can also be derived from genetics or omics. The clinical parameter may also represent likelihood of a meaningful clinical outcome, such as response to a specific or general therapy, or likelihood of disease progression or regression.

A cell identification component 122 identifies, for each of a plurality of cells within the image, a representative point to provide a plurality of representative points for each of the plurality of medium-scale epithelial components. It will be appreciated that the image will contain a plurality of medium-scale epithelial components, with each medium-scale epithelial component containing a plurality of cells. The plurality of cells located by the cell identification component 122 can be constrained to only locate representative points for cells within the boundaries of the medium-scale epithelial components, or all cells within the image can be assigned a representative point. It will be appreciated that a representative point for a cell can be any landmark that can be readily located to indicate the position of a given cell within the image. This can include a geometric object with the medium-scale epithelial component having associated coordinates. An appropriate landmark for the cell can be determined, for example, from various features within the image, derived from the hue, saturation, or intensity of colors within the image, grayscale brightness, texture, edge detection, or local patterns or clusters of these parameters. The landmark can also be obtained from a corresponding image and transferred by registration. In one implementation, the cell identification component 122 identifies the representative point for each cell as a center of either the cell or the nucleus of the cell.

A graph constructor 124 constructs, for each of a subset of the plurality of medium-scale epithelial components, a graph connecting a subset of the plurality of representative points. The graph constructed by the graph constructor 124 can include, for example, one or more of a Voronoi tessellation, a Delaunay triangulation, a minimum spanning tree, a minimum distance path passing through each of the plurality of representative points exactly once, a Gabriel graph, a relative neighborhood graph, a beta-skeleton, an O'Callaghan Neighborhood graph, a Cell graph, a Johnson-Mehl Tessellation, an Attributed relational graph, a line graph, a Random geometric graph, an Ulam tree, and a k-nearest neighbor graph.

A feature extractor 126 determines, for each of the subset of medium-scale epithelial components, a plurality of classification features from the graph and its component elements constructed from the medium-scale epithelial component. The characteristics can result from the mathematical representation of the graph, such as degree or clustering coefficient. The representation of the graph as a matrix results in the class of spectral characteristics, such as eigenvalues or a Cheeger constant. Another class of characteristics results from the Euclidean geometry of the underlying point cloud. For example, distances between points or size of enclosed surfaces. Statistical descriptors can be used for globally describing these attributes of individual elements. These include mean, standard deviation, minimum to maximum ratio, disorder, skewness, kurtosis and higher-order descriptors. In addition, co-occurrence matrices can be constructed and evaluated with Haralick features, for example. All these feature classes can be used to divide the graph into subgraphs. For these subgraphs further characteristics can be determined which can also be evaluated statistically or with co-occurrence matrices. In general, the plurality of classification features can include, for example, measures of statistical dispersion (e.g., variance, standard deviation, percentile values, range, mean absolute difference, relative mean absolute difference, interquartile range, etc.) and/or a measures of central tendency (e.g., arithmetic mean, geometric mean, harmonic mean, quadratic mean, a truncated or Winsorized version of any of these means, trimean, midrange, midhinge, median, or mode), of various features within the graphs. These can include, for example, absolute lengths of line segments within the graph, ratios of lengths of line segments within the graph, areas of regions or polygons within the graph, angles between pairs of line segments, regions, or polygons within the graph, angles between line segments, regions, or polygons and a reference vector, aggregate lengths of line segments within the graph, and numbers of regions or line segments within the graph.

Figure 2:
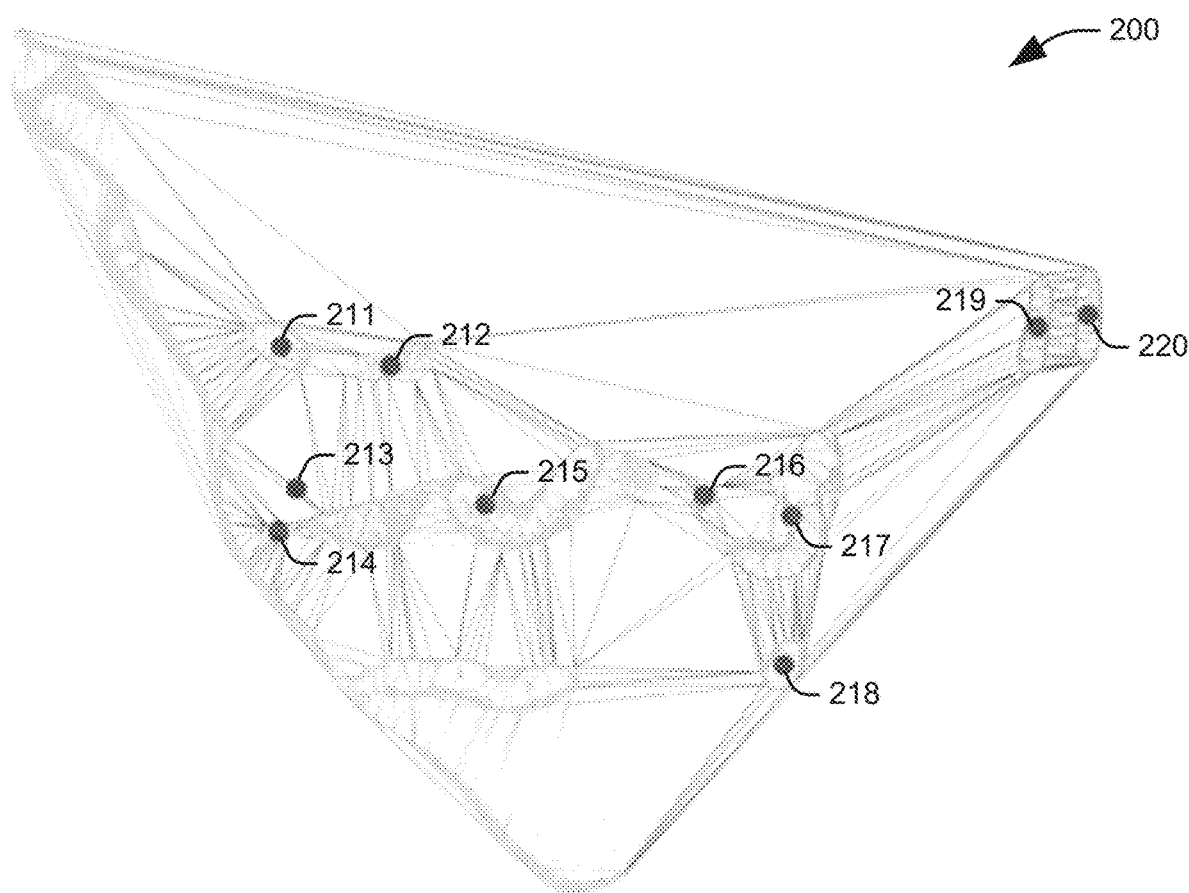
FIG. 2 shows a gland neighborhood graph connecting centroids and reference points of multiple nearby glands.

Many biological processes in solid tissue are geographically expansile (e.g., enlarging neoplastic clones) or local (e.g., point of infection), such that a regional spatial neighborhood of glands are likely to share a common biologic property. In another implementation, an algorithm applied at a machine learning model 128 may be weighted by, or combined with, additional algorithms prepared from graphs joining representative points of multiple nearby glands. The clinical parameter assigned to a specific "reference" gland may thus be modified or weighted by a parameter representing the local neighborhood of glands. The local neighborhood changes with each reference gland and refers to a population of nearby glands present within a specified distance or hierarchy of distance (e.g., first closest gland, second closest gland, third closest gland) relative to the reference gland. The gland neighborhood is unique for each reference gland but may overlap between reference glands. In one manifestation, one representative point for each neighborhood gland is used to create a new graph classified by the machine learning model according to the clinical parameter, and the class probability assignment for the neighborhood used to modify the clinical parameter class of the reference gland. In another manifestation, variables from a single reference gland are combined with variables from the gland neighborhood to create an integrated machine learning model for classification of the reference gland. FIG. 2 shows a gland neighborhood graph 200 connecting centroids 211-220 and reference points of multiple nearby glands.

The machine learning model 128 assigns a clinical parameter to each medium-scale epithelial component according to the extracted plurality of classification features. The machine learning model 128 can utilize one or more pattern recognition algorithms, implemented, for example, as classification and regression models, each of which analyze the extracted features to assign a clinical parameter to the medium-scale epithelial component. Where multiple classification and regression models are used, the machine learning model 128 can include an arbitration element that can be utilized to provide a coherent result from the various algorithms. Depending on the outputs of the various models, the arbitration element can simply select a class from a model having a highest confidence, select a plurality of classes from all models meeting a threshold confidence, select a class via a voting process among the models, or assign a numerical parameter based on the outputs of the multiple models. Alternatively, the arbitration element can itself be implemented as a classification model that receives the outputs of the other models as features and generates one or more output classes for the patient. A classification can also be performed across multiple stages. In one example, an a priori probability can be determined for a clinical parameter without the features extracted for the medium-scale epithelial component, for example, from other image features extracted for the medium-scale epithelial component, such as color content or texture. A second stage of the model can use the features to generate a value for the clinical parameter. A known performance of the second stage of the machine learning model, for example, defined as values for the specificity and sensitivity of the model, can be used to update the a priori probability given the output of the second stage.

The machine learning model 128, as well as any constituent models, can be trained on training data representing the various classes or dependent variables of interest. The training process of the machine learning model 128 will vary with its implementation, but training generally involves a statistical aggregation of training data into a set of parameters for the model. Any of a variety of techniques can be utilized for the models, including support vector machines, regression models, self-organized maps, k-nearest neighbor classification or regression, fuzzy logic systems, data fusion processes, boosting and bagging methods, rule-based systems, random forests, recursive partitioning, or artificial neural networks, including fully connected and convolution neural networks.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. An SVM classifier utilizes a user-specified kernel function to organize training data within a defined feature space. In the most basic implementation, the kernel function can be a radial basis function, although the systems and methods described herein can utilize any of a number of linear or non-linear kernel functions.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

A k-nearest neighbor model populates a feature space with labelled training samples, represented as feature vectors in the feature space. In a classifier model, the training samples are labelled with their associated class, and in a regression model, the training samples are labelled with a value for the dependent variable in the regression. When a new feature vector is provided, a distance metric between the new feature vector and a subset of the feature vectors representing the labelled training samples is generated. The labelled training samples are then ranked according to the distance of their feature vectors from the new feature vector, and a number, k, of training samples having the smallest distance from the new feature vector are selected as the nearest neighbors to the new feature vector.

In one example of a classifier model, the class represented by the most labelled training samples in the k nearest neighbors is selected as the class for the new feature vector. In another example, each of the nearest neighbors can be represented by a weight assigned according to their distance from the new feature vector, with the class having the largest aggregate weight assigned to the new feature vector. In a regression model, the dependent variable for the new feature vector can be assigned as the average (e.g., arithmetic mean) of the dependent variables for the k nearest neighbors. As with the classification, this average can be a weighted average using weights assigned according to the distance of the nearest neighbors from the new feature vector. It will be appreciated that k is a metaparameter of the model that is selected according to the specific implementation. The distance metric used to select the nearest neighbors can include a Euclidean distance, a Manhattan distance, or a Mahalanobis distance.

A regression model applies a set of weights to various functions of the extracted features, most commonly linear functions, to provide a continuous result. In general, regression features can be categorical, represented, for example, as zero or one, or continuous. In a logistic regression, the output of the model represents the log odds that the source of the extracted features is a member of a given class. In a binary classification task, these log odds can be used directly as a confidence value for class membership or converted via the logistic function to a probability of class membership given the extracted features.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used, but a continuous parameter can be computed according to a number of decision trees that select a given task. It will be appreciated that the number of trees, as well as a number of features used to generate trees, can be selected as metaparameters for the random forest model.

Regardless of the specific model employed, the clinical parameter generated at the machine learning model 128 can be provided to a user at an associated display (not shown) or stored on the non-transitory computer readable medium 120 for analysis by another automated system (not shown). In one implementation, the executable instructions include a user interface (not shown) that generates a spatial mapping of the subset of the plurality of medium-scale epithelial components at an associated display, with each medium-scale epithelial component in the spatial mapping represented by an indicator indicative of the clinical parameter assigned to the medium-scale epithelial component. In one example, where the clinical parameter is a categorical parameter, the class of each medium-scale epithelial component can be indicated as a color, with each of a plurality of colors representing an associated one of a plurality of output classes. In this instance, a confidence associated with the clinical parameter can be indicated as a one of a saturation and a brightness of the color, shape, or size of the symbol associated with the clinical parameter. Where the clinical parameter is continuous, the clinical parameter can be displayed, for example, in a heat map approach in which one or more of the hue, saturation, intensity, shape or size of the image can be varied with the clinical parameter. In either instance, the spatial mapping can be displayed independently or as an overlay on the image.

Figure 3:
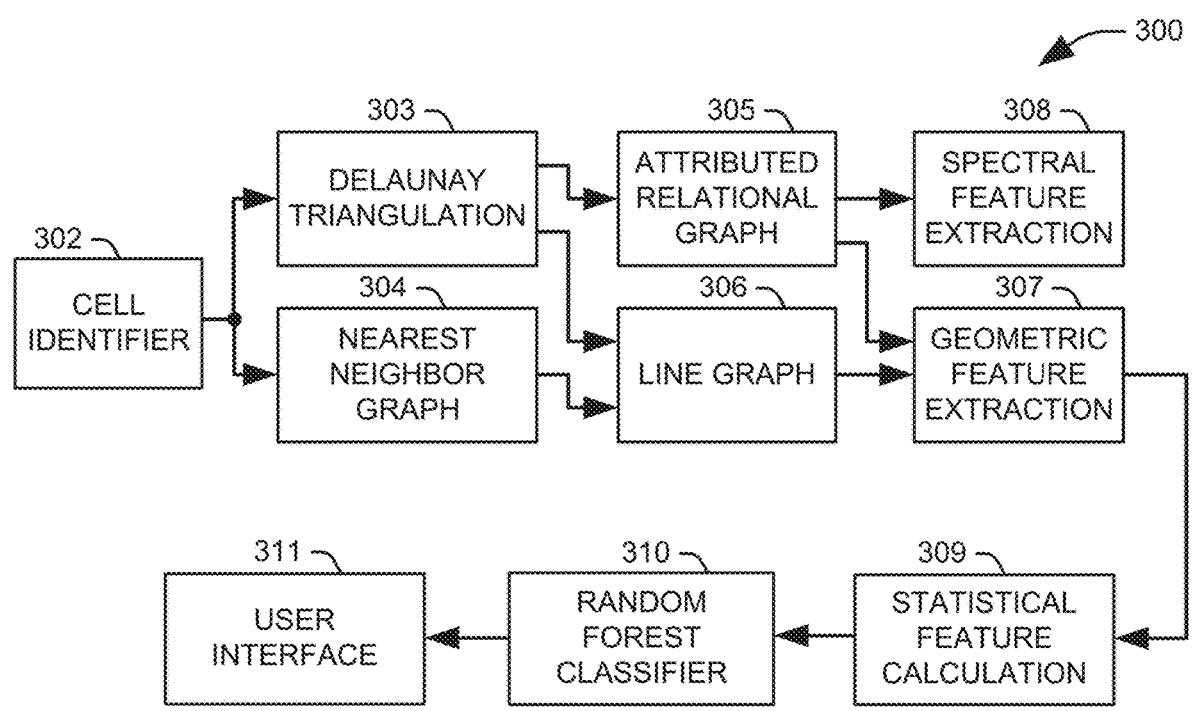
FIG. 3 illustrates an example implementation of an image analysis system in accordance with an aspect of the present invention.

FIG. 3 illustrates an example implementation of an image analysis system 300 in accordance with an aspect of the present invention. It will be appreciated that the image analysis system 300 can be implemented as a series of functional blocks 302-311 stored on a non-transitory computer readable medium and executed by an associated processor. In the illustrated example, the image analysis system 200 receives an image of a stained histological slide of tissue having a glandular epithelial component, such as breast tissue or endometrial tissue, and determines, for at least a subset of glands within the image, if each gland is benign or neoplastic. To this end, the image is provided to a cell identification component 302 that identifies, for each of a plurality of cells within the image, a representative point to provide a plurality of representative points for each of the plurality of glands. In the illustrated implementation, the representative point for each cell is a geometric centroid of the cell nucleus.

A Delaunay triangulation component 303 constructs at least a Delaunay triangulation for a subset of the glands using the representative points for each gland. For a given set of points in a plane, the Delaunay triangulation is a triangulation such that no point is inside the circumcircle of any triangle in the triangulation. A Delaunay triangulation maximizes the minimum angle of all the angles of the triangles in the triangulation. To avoid classifying glands for which limited information is available, the Delaunay triangulation can be constructed only those glands for which a threshold number of representative points are available. The threshold number of representative points can vary with the application and with the imaging modality. In one example, the threshold number of points can be determined dynamically, with glands having a number of points below a certain percentile of all glands (e.g., in a bottom quartile) being excluded. The inventors have found this to significantly increase the accuracy of classification of the glands. It will be appreciated that a Voronoi diagram can be readily constructed from a completed Delaunay triangulation, as the circumcenters of Delaunay triangles are the vertices of the Voronoi diagram. Accordingly, in one example, the Delaunay triangulation component 303 can also construct a Voronoi diagram for each of the subset of glands.

A nearest neighbor graph component 304 constructs a graph in which each representative point is connected to its four nearest neighbors, although it will be appreciated that the number of nearest neighbors used can be a tunable parameter for the system. An attributed relational graph component 305 generates an attributable relational graph from the Delaunay triangulation and a line graph component 306 generates a line graph representing the Delaunay triangulation and the nearest neighbor graph.

A geometric feature extractor 307 determines, for each of the subset of glands, a plurality of classification features from the graphs constructed for the gland. In the illustrated implementation, the plurality of classification features can include, for example, measures of statistical dispersion and measures of central tendency for lengths of line segments within the Delaunay triangulation, angles in triangles (e.g., minimum angles) formed in the Delaunay triangulation, and, where a Voronoi diagram is constructed, areas of regions in the Voronoi diagram. A spectral feature extractor 308 uses a representation of the attributed relational graph as a matrix results in the class of spectral characteristics, such as eigenvalues or a Cheeger constant. A statistical feature extractor 309 extracts measures of statistical dispersion and measures of central tendency for measured derived from these values, such as aggregate values or ratios between values.

A random forest classifier 310 assigns an output class, selected from a "neoplastic" class, a "benign" class, and an "unknown" class to each gland according to the extracted plurality of classification features. In the illustrated implementation, the random forest classifier 310 selects randomly from a group of approximately seventy-five features drawn from the Delaunay triangulation and Voronoi diagram constructed for the gland and generates around five hundred decision trees to classify each gland. Each decision tree classifies the gland as neoplastic or benign. If either class is selected by a threshold number of the classifiers, the class is assigned to the gland. Otherwise, the gland can be classified as unknown. The specific threshold value for each class will vary with the specific implementation. In one implementation, where an unknown class is not used, the threshold can be set at majority (i.e., half plus one) of the decision trees used or at a value intended to account for the a priori likelihood that the gland belongs to a given class. Otherwise, the threshold can be set to reflect a desired level of confidence in the classification, with subthreshold results classified as the unknown class. It will be appreciated that the two classes can have different threshold values.

In one implementation, the threshold number of decision trees necessary for a given class, such as the neoplastic class, can be varied dynamically with the results of the classification to ensure that at least a threshold number of glands are found to belong to the specified class. It will be appreciated that the system 300 is intended to facilitate review of the histological slide by a human operator. Since the human reviewer will look for concentrations of malignant glands, scattered random false positives are unlikely to cause any confusion. Even concentrations of false positives in classification of the individual gland can be compensated for by the human review.

The classifications of the individual glands are provided to a user interface 311 that displays a spatial mapping of representations of the clinical parameter for the subset of the plurality of glands. The spatial mapping can include, for example, a data cloud composed of one symbol per gland coregistered to anatomic histology coordinates. Where the clinical parameter is categorical, the category to which each gland belongs can be represented, for example, by a specific icon, color, pattern, or other visible indicator. Where the clinical parameter is continuous, the clinical parameter can be indicated, for example, by color or grayscale brightness, in a heat map arrangement, an intensity or brightness of a region or icon, or by a size of an icon. In one implementation, the indication of the clinical parameter can be displayed as an overlay with the original image to guide analysis of the image by the pathologist.

Figure 4:
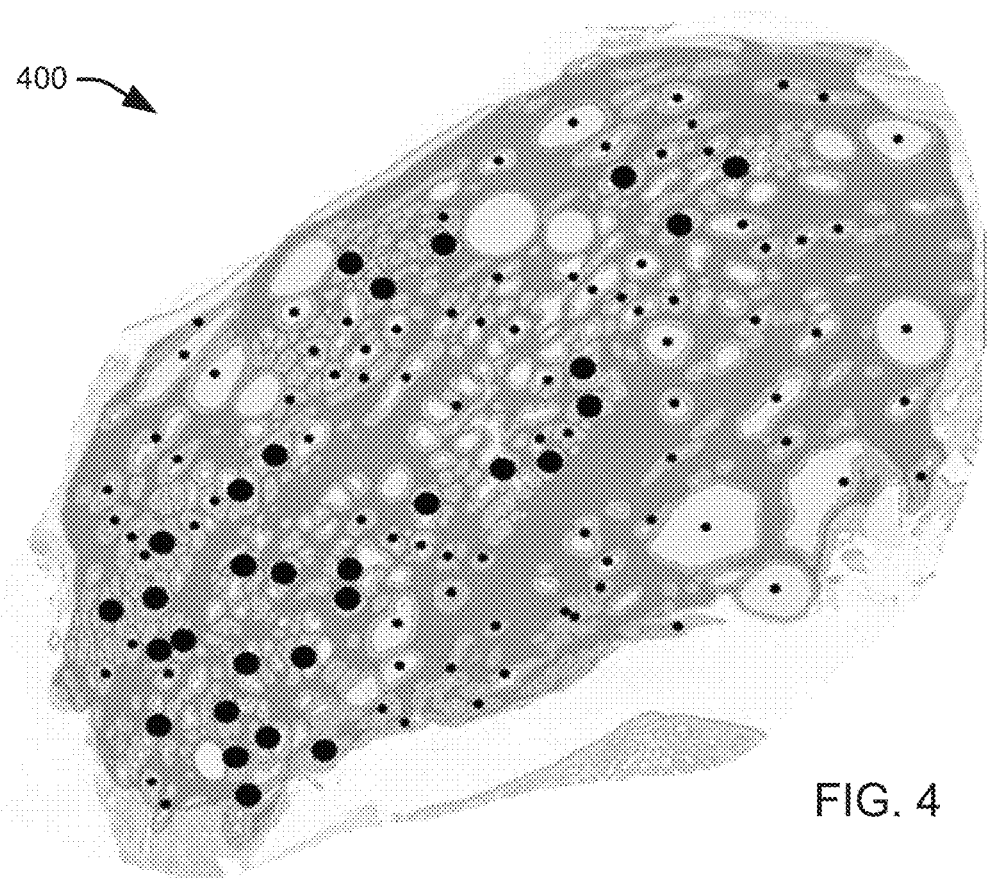
FIG. 4 illustrates one example of a spatial mapping of clinical parameters, illustrating classification of glands, in accordance with an aspect of the present invention.

FIG. 4 illustrates one example of a spatial mapping 400 of clinical parameters in accordance with an aspect of the present invention. In the illustrated mapping 400, neoplastic glands are represented as large circles, while benign glands are represented as small circles. As can be seen in the image, the regions that might contain a lesion are immediately apparent to a human observer. Accordingly, a large image, such as a histological slide, can be reviewed at low magnification in combination with the spatial mapping, and the regions indicated by the spatial mapping of clinical parameters can be reviewed in further detail by a pathologist. A cloud display of coordinate-registered data elements, as shown, maintains its perceived regional concentration of specific clinical parameters even when some glands are excluded from the analysis, or a degree of class admixture occurs locally.

Figure 5:
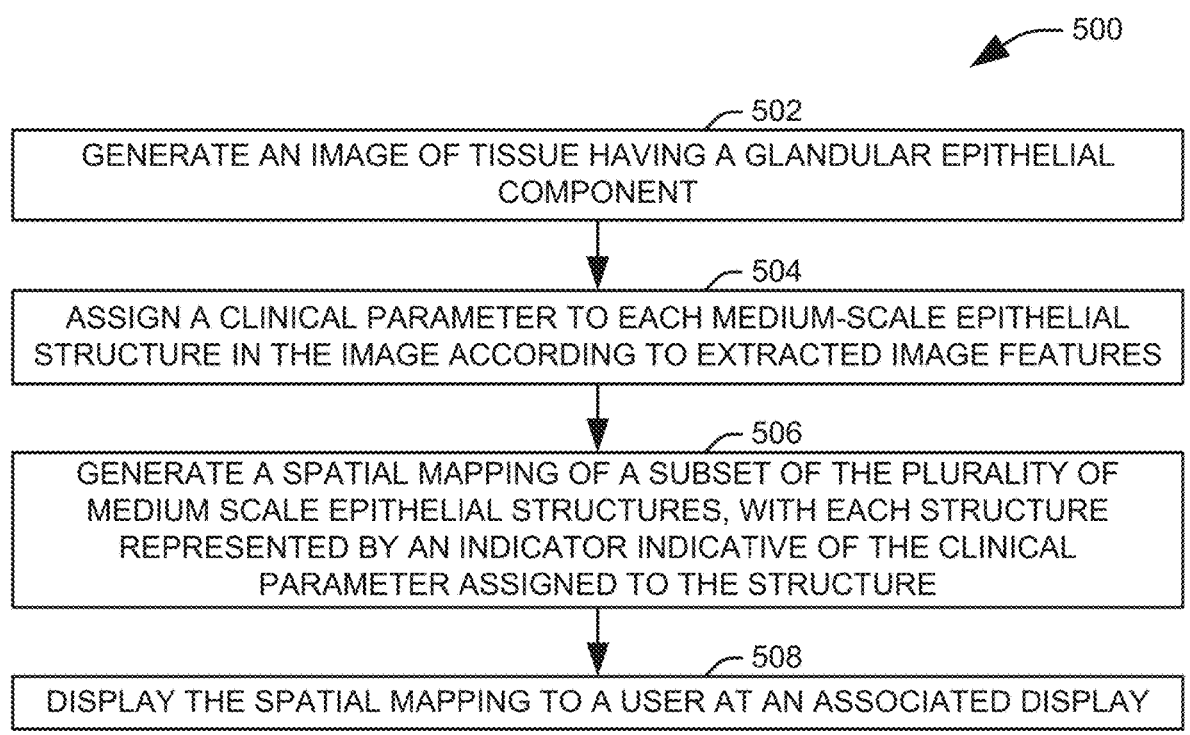
FIG. 5 illustrates a method for generating an image of tissue having a glandular epithelial component.

FIG. 5 illustrates a method 500 for generating an image of tissue having a glandular epithelial component. At 502, generating an image of tissue having a glandular epithelial component. In one example, the image is generated as a digital microscopy image of a stained histological slide. In another implementation, the image is generated as an X-ray microtomographic image. At 504, a clinical parameter is assigned to each of a subset of the medium-scale epithelial components according to features extracted from the image. The subset of medium-scale epithelial components can include, in one example, only for medium-scale epithelial components for which the number of representative points in the plurality of representative points for the medium-scale epithelial component exceeds a threshold value. In one implementation, representative points are selected to provide a plurality of representative points for each medium-scale epithelial component, a graph is constructed connecting the representative points, features are extracted from the graph, and a clinical parameter is assigned to the medium-scale epithelial component according to the extracted features.

At 506, a spatial mapping is generated for a subset of the plurality of medium-scale epithelial components, with each medium-scale epithelial component in the spatial mapping represented by an indicator indicative of the clinical parameter assigned to the medium-scale epithelial component. In one example, where the clinical parameter is a categorical parameter, the indicator indicative of the clinical parameter assigned to the medium-scale epithelial component is provided as a color for each category. In this example, a confidence associated with the clinical parameter can be indicated as a one of a saturation and a brightness of the color associated with the clinical parameter. In another example, where the clinical parameter is a categorical parameter, the indicator indicative of the clinical parameter assigned to the medium-scale epithelial component is provided as icons representing the various categories. In still another example, where the clinical parameter is a continuous parameter, the indicator indicative of the clinical parameter assigned to the medium-scale epithelial component is implemented as a heat map, in which the value of the clinical parameter is represented as at least one of a hue, saturation, or brightness in the spatial mapping. At 508, the spatial mapping is displayed to a user at an associated display. In one example, the spatial mapping is displayed to the user as an overlay on the image.

Figure 6:
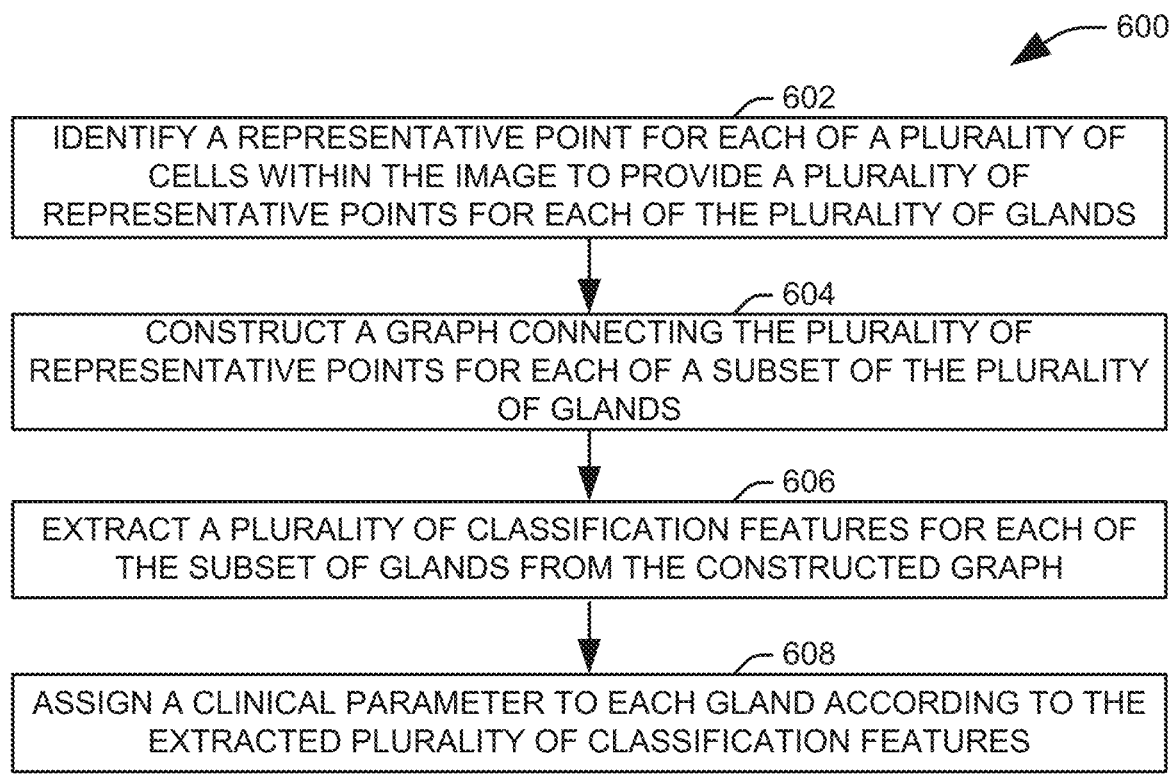
FIG. 6 illustrates a method for assigning a clinical parameter to glands within a captured image.

FIG. 6 is a method 600 for assigning a clinical parameter to glands within a captured image. At 602 a representative point is identified for each of a plurality of cells within the image to provide a plurality of representative points for each of the plurality of glands. In one implementation, the representative point for each cell is a center of the cell. In another implementation, the representative point for each cell is a center of the nucleus of the cell. At 604, a graph connecting the plurality of representative points is constructed for each of a subset of the plurality of glands. The subset of the plurality of glands can be selected to exclude glands for which a subthreshold number of representative points are available. The constructed graph can include, for example, one or more of a Voronoi tessellation, a Delaunay triangulation, a minimum spanning tree, a minimum distance path passing through each of the plurality of representative points exactly once, a Gabriel graph, a relative neighborhood graph, and a k-nearest neighbor graph.

At 606, a plurality of classification features are generated for each of the subset of glands from the graph constructed for the gland. In one example, the features include measures of deviation and/or measures of central tendency of lengths of line segments within the constructed graph. In another example, the features include measures of deviation and/or measures of central tendency of angles between line segments within the constructed graph. At 608, a clinical parameter is assigned to each gland according to the extracted plurality of classification features, for example, using a machine learning model. For example, a confidence value or similar parameter can be assigned to each gland using the machine learning model and compared to a threshold confidence to assign the gland into one of a plurality of classes. In one implementation, this is performed dynamically to ensure that a threshold number of glands are assigned to a given class. In this implementation, it can be determined if a threshold number of glands in the subset of the plurality of glands have been assigned to the given class using a first threshold confidence, and each gland of the subset of the plurality of glands can be reclassified with a second threshold confidence if the threshold number of glands has not been assigned to the given class.

Figure 7:
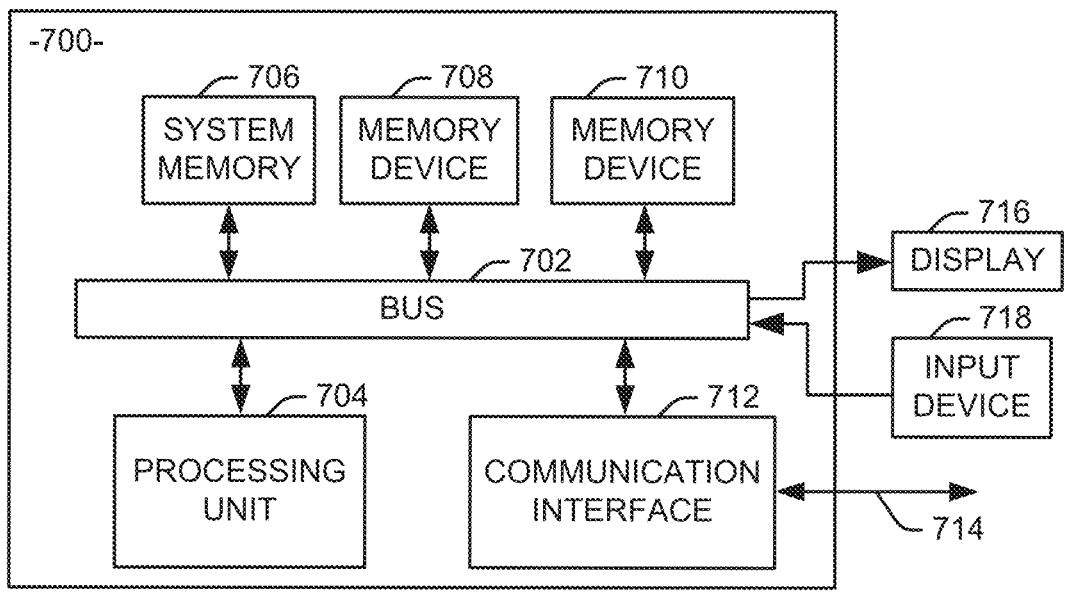
FIG. 7 illustrates a schematic block diagram illustrating an exemplary system of hardware components capable of implementing examples of systems and methods disclosed herein.

FIG. 7 is a schematic block diagram illustrating an exemplary system 700 of hardware components capable of implementing examples of the systems and methods disclosed in FIGS. 1-5. The system 700 can include various systems and subsystems. The system 700 can be a personal computer, a laptop computer, a workstation, a computer system, an appliance, an application-specific integrated circuit (ASIC), a server, a server blade center, a server farm, etc.

The system 700 can includes a system bus 702, a processing unit 704, a system memory 706, memory devices 708 and 710, a communication interface 712 (e.g., a network interface), a communication link 714, a display 716 (e.g., a video screen), and an input device 718 (e.g., a keyboard and/or a mouse). The system bus 702 can be in communication with the processing unit 704 and the system memory 706. The additional memory devices 708 and 710, such as a hard disk drive, server, stand-alone database, or other non-volatile memory, can also be in communication with the system bus 702. The system bus 702 interconnects the processing unit 704, the memory devices 706-710, the communication interface 712, the display 716, and the input device 718. In some examples, the system bus 702 also interconnects an additional port (not shown), such as a universal serial bus (USB) port.

The processing unit 704 can be a computing device and can include an application-specific integrated circuit (ASIC). The processing unit 704 executes a set of instructions to implement the operations of examples disclosed herein. The processing unit can include a processing core.

The additional memory devices 706, 708 and 710 can store data, programs, instructions, database queries in text or compiled form, and any other information that can be needed to operate a computer. The memories 706, 708 and 710 can be implemented as computer-readable media (integrated or removable) such as a memory card, disk drive, compact disk (CD), or server accessible over a network. In certain examples, the memories 706, 708 and 710 can comprise text, images, video, and/or audio, portions of which can be available in formats comprehensible to human beings. Additionally or alternatively, the system 700 can access an external data source or query source through the communication interface 712, which can communicate with the system bus 702 and the communication link 714.

In operation, the system 700 can be used to implement one or more parts of a sequence alignment system or method in accordance with the present invention. Computer executable logic for implementing the sequence alignment resides on one or more of the system memory 706, and the memory devices 708, 710 in accordance with certain examples. The processing unit 704 executes one or more computer executable instructions originating from the system memory 706 and the memory devices 708 and 710. The term "computer readable medium" as used herein refers to any medium that participates in providing instructions to the processing unit 704 for execution, and it will be appreciated that a computer readable medium can include multiple computer readable media each operatively connected to the processing unit.

Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to, portable or fixed storage devices, optical storage devices, wireless channels, and/or various other storage mediums capable of storing that contain or carry instruction(s) and/or data.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. A system comprising:
    an digital microscope that provides an image of tissue having a glandular epithelial component as a whole slide image of a stained histological slide, the image representing a plurality of medium-scale epithelial components;
    a processor; and
    a non-transitory computer readable medium storing instructions executable by the processor, the executable instructions comprising:
        a cell identification component that identifies, for each of a plurality of cells within the image, a representative point to provide a plurality of representative points for each of the plurality of medium-scale epithelial components;
        a graph constructor that constructs, for each of a subset of the plurality of medium-scale epithelial components, a graph connecting the plurality of representative points;
        a feature extractor that determines, for each of the subset of medium- scale epithelial components, a plurality of classification features from the graph constructed for the medium-scale epithelial component, the feature extractor extracting the plurality of classification features only for medium-scale epithelial components for which a number of representative points in the plurality of representative points for the medium-scale epithelial component exceeds a threshold value, such that the subset of the plurality of medium-scale epithelial components is a proper subset; and
        a machine learning model that assigns a clinical parameter to each medium-scale epithelial component according to the extracted plurality of classification features.

2. The system of claim 1, wherein the cell identification component identifies the representative point for each cell as a center of the cell.

3. The system of claim 1, wherein the cell identification component identifies the representative point as a center of a nucleus of the cell, or a subcellular structure.

4. The system of claim 1, wherein the graph constructor constructs, for each of the subset of the plurality of medium-scale epithelial components, at least one of a Voronoi tessellation, a Delaunay triangulation, a minimum spanning tree, a minimum distance path passing through each of the plurality of representative points exactly once, a Gabriel graph, a relative neighborhood graph, and a k-nearest neighbor graph.

5. The system of claim 4, wherein the feature extractor determines at least one of the plurality of classification features as one of a measure of deviation and a measure of central tendency of lengths of line segments within the constructed one of the Voronoi tessellation, the Delaunay triangulation, the minimum spanning tree, the minimum distance path passing through each of the plurality of representative points exactly once, the Gabriel graph, the relative neighborhood graph, and the k-nearest neighbor graph.

6. The system of claim 4, wherein the feature extractor determines at least one of the plurality of classification features as one of a measure of deviation and a measure of central tendency of angles between line segments within the constructed one of the Voronoi tessellation, the Delaunay triangulation, the minimum spanning tree, the minimum distance path passing through each of the plurality of representative points exactly once, the Gabriel graph, the relative neighborhood graph, and the k-nearest neighbor graph.

7. The system of claim 1, the executable instructions further comprising a user interface that generates a spatial mapping of the subset of the plurality of medium-scale epithelial components at an associated display, with each medium-scale epithelial component in the spatial mapping represented by an indicator indicative of the clinical parameter assigned to the medium-scale epithelial component.

8. A method comprising:
    generating an image of tissue having a glandular epithelial component at a digital microscope as a whole slide image of a stained histological slide, the image representing a plurality of medium-scale epithelial components;

identifying, for each of a plurality of cells within the image, a representative point to provide a plurality of representative points for each of the plurality of medium-scale epithelial components;

constructing, for each of a subset of the plurality of medium-scale epithelial components, a graph connecting the plurality of representative points;

extracting a plurality of classification features for each of the subset of medium- scale epithelial components from the graph constructed for the medium-scale epithelial component; and assigning a clinical parameter to each medium-scale epithelial component according to the extracted plurality of classification features, wherein assigning the clinical parameter to each of the subset of the plurality of medium-scale epithelial components according to the extracted plurality of classification features comprises:

generating a confidence value for each medium-scale epithelial component of the subset of the plurality of medium-scale epithelial components;

comparing the confidence value to a first threshold confidence to determine if each medium-scale epithelial component of the subset of the plurality of medium-scale epithelial components belongs to a given class;

determining if a threshold number of medium-scale epithelial components in the subset of the plurality of medium-scale epithelial components have been assigned to the given class; and reclassifying each medium-scale epithelial component of the subset of the plurality of medium-scale epithelial components with a second threshold confidence if the threshold number of medium-scale epithelial components has not been assigned to the given class.

9. The method of claim 8, further comprising:

generating a spatial mapping of the subset of the plurality of medium-scale epithelial components, with each medium-scale epithelial component in the spatial mapping represented by an indicator indicative of the clinical parameter assigned to the medium-scale epithelial component; and displaying the spatial mapping to a user at an associated display.

* * * * *